United States Patent
Balobeck

(10) Patent No.: US 7,173,955 B2
(45) Date of Patent: Feb. 6, 2007

(54) LASER STIMULATED SYMPATHETIC VIBRATION OF MOLECULAR STRUCTURE OF A BODY

(76) Inventor: Joseph J. Balobeck, 200 Dinsmore Ave., Pittsburgh, PA (US) 15205

( * ) Notice: Subject to any disclaimer, the term of this patent is extended or adjusted under 35 U.S.C. 154(b) by 307 days.

(21) Appl. No.: 10/230,747

(22) Filed: Aug. 29, 2002

(65) Prior Publication Data

US 2003/0043377 A1    Mar. 6, 2003

Related U.S. Application Data

(60) Provisional application No. 60/316,477, filed on Aug. 31, 2001.

(51) Int. Cl.
*H01S 3/091*    (2006.01)

(52) U.S. Cl. .......................... 372/70; 372/20

(58) Field of Classification Search ................ 372/92, 372/20, 75, 34, 70, 71
See application file for complete search history.

(56) References Cited

U.S. PATENT DOCUMENTS

| | | | | |
|---|---|---|---|---|
| 5,253,102 A | * | 10/1993 | Okazaki | 359/328 |
| 5,383,209 A | * | 1/1995 | Hwang | 372/34 |
| 5,854,802 A | * | 12/1998 | Jin et al. | 372/22 |
| 5,905,748 A | * | 5/1999 | Xie | 372/22 |

* cited by examiner

*Primary Examiner*—Minsun Oh Harvey
*Assistant Examiner*—Tuan N. Nguyen
(74) *Attorney, Agent, or Firm*—The Webb Law Firm

(57) ABSTRACT

A laser system outputs a laser light which is directed toward an object. The laser light has a frequency corresponding to the sympathetic or natural vibration frequency of molecules forming the object. The laser light is controlled so that in response to interaction with the object, the laser light forces the molecules of the object to vibrate at their sympathetic or natural vibration frequency thereby causing a thermal resistance of the object to increase whereupon a flow of thermal energy through the object is obstructed.

12 Claims, 1 Drawing Sheet

LASER STIMULATED SYMPATHETIC VIBRATION OF MOLECULAR STRUCTURE OF A BODY

CROSS REFERENCE TO RELATED APPLICATION

Figure 1:
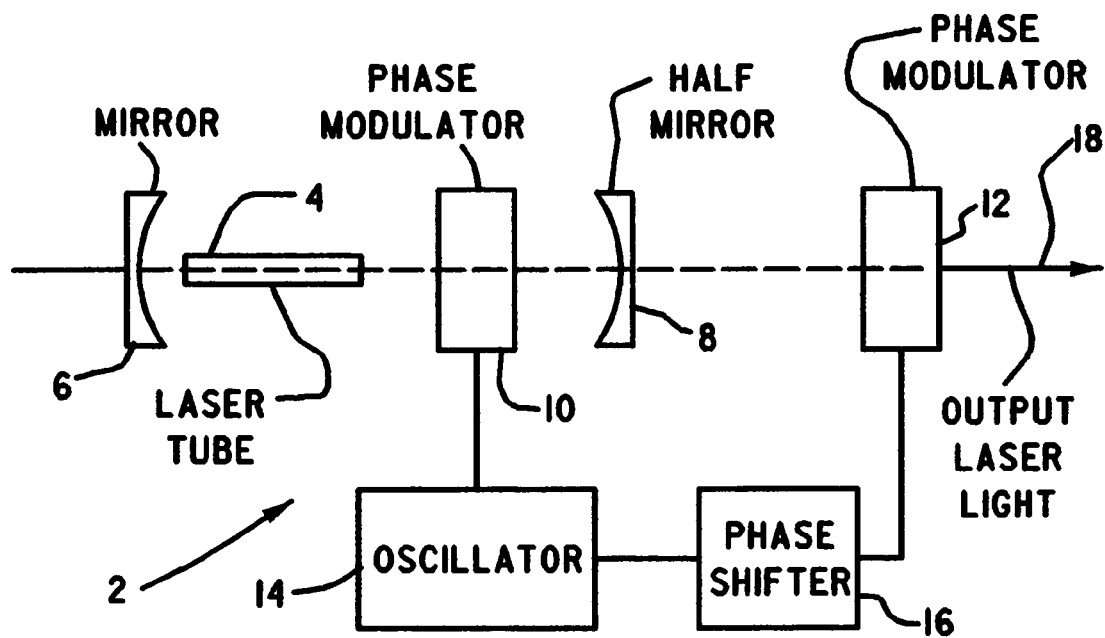

The present invention claims priority from U.S. Provisional Patent Application Ser. No. 60/316,477, filed Aug. 31, 2001, entitled "Laser Stimulated Sympathetic Vibration Of Molecular Structure Of A Body".

BACKGROUND OF THE INVENTION

1. Field of the Invention

The present invention relates to stimulating an object, such as a sheet of glass, in a manner to obstruct the flow of energy therethrough.

2. Description of the Related Art

Presently, one of the primary areas where heat energy enters a structure is through windows. To this end, energy in the form of radiation, conduction and/or convection can propagate through the glass of a window which separates the interior of the structure from the exterior of the structure. Attempts at rejecting this energy include forming or installing ultraviolet filters in or on the window to reflect ultraviolet radiation and including a shade on or adjacent the window. These attempts, however, only address radiated energy, not energy transferred by conduction or convection.

It is, therefore, an object of the present invention to overcome the above problem and others by providing an apparatus and method for stimulating the molecules of a sheet of glass of a window to obstruct the flow of energy therethrough via radiation, conduction or convection.

SUMMARY OF THE INVENTION

The invention is a method of obstructing a flow of energy through an object. The method includes providing a signal source that produces an output signal having a frequency the same or substantially the same as a sympathetic or natural vibration frequency of molecules forming the object. The output signal is directed toward the object whereupon, in response to interaction with the output signal, the molecules of the object vibrate at or near their sympathetic vibration frequency thereby obstructing a flow of energy through the object.

The object can be a sheet of glass having a pair of oppositely facing surfaces. The signal source can include a laser and the output signal can be a laser light.

The output signal is controlled so that a phase of the output signal is in phase with the phase of the molecules of the object when the output signal interacts with the object.

The step of directing the output signal toward the object includes causing the laser light to propagate through the sheet of glass between the surfaces in a direction substantially parallel to at least one of the surfaces whereupon the flow of energy is obstructed from flowing between the surfaces of the sheet of glass.

The energy that is obstructed from flowing includes at least one of radiation, conduction and convection.

The laser light produces in the sheet of glass a blanket oscillation field that extends through the sheet of glass parallel to at least one of the surfaces thereof.

The signal source can include a laser tube positioned to propagate a laser light from opposite ends thereof toward a fully reflective mirror and a half-reflective mirror. A phase modulator can be positioned in the path of the laser light between the laser tube and the half-reflective mirror. A second phase modulator can be positioned in the path of the laser light on a side of the half-reflective mirror opposite the first modulator and a control means can be provided for controlling the first and second phase modulators whereupon the laser light propagating from the second phase modulator away from the half-reflective mirror is in phase with the phase of the molecules forming the object when the laser light interacts with the object.

The control means can include an oscillator for producing an oscillator signal and a phase shifter for phase shifting the oscillator signal. The first and second phase modulators are responsive to the oscillator signal and the phase shifted oscillator signal, respectively, for adjusting the laser light whereupon the phase of the laser light propagating from the second phase modulator away from the half-reflective mirror is in phase with the molecules forming the object when the laser light interacts therewith.

The invention is also a system for obstructing a flow of energy. The system includes an object interposed between a heat source and a heat sink, where the heat source is at a higher temperature than the heat sink. The object has a first thermal resistance to the flow of heat between the heat source and the heat sink. The system also includes means for urging molecules of the object to vibrate at or substantially at their natural vibration frequency whereupon, in response to said vibration, the thermal resistance of the object increases to a second thermal resistance.

The exciting means can be a super mode-locking laser that outputs a laser light having the same frequency as the natural vibration frequency of the molecules of the object. The exciting means can further include means for reflecting at least part of the laser light and means for adjusting a phase of the laser light whereupon a phase of the laser light interacting with the object is in phase with the phase of the molecules of the object. The adjusting means can include an oscillator for outputting an oscillator signal and a phase modulator responsive to the oscillator signal. The reflecting means can include a full mirror positioned at one end of the laser for reflecting light output thereby back into the laser and a half-mirror positioned at the other end of the laser for reflecting part of the light output thereby back into the laser and for partially passing laser light impinging thereon.

DETAILED DESCRIPTION OF THE DRAWINGS

Figure 2:
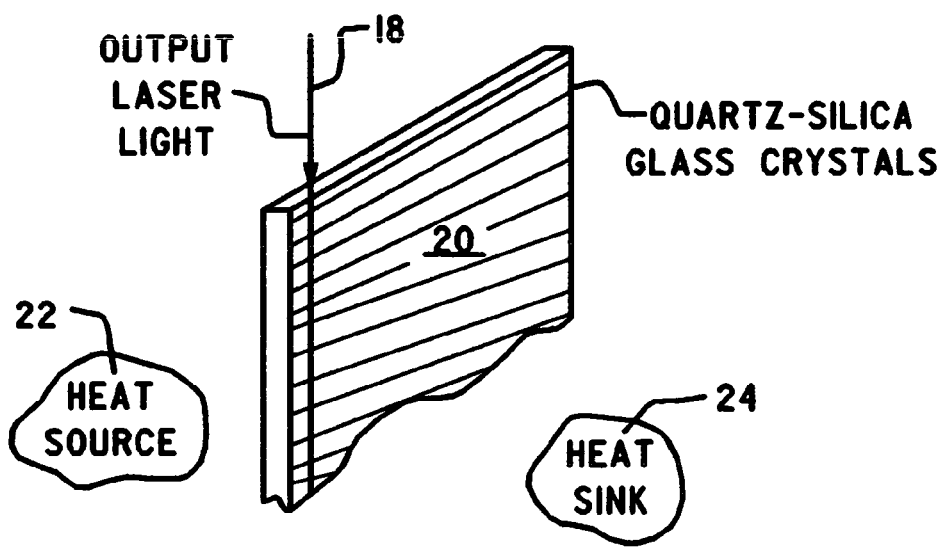

FIG. 1 is a diagrammatic illustration of a laser system utilized to implement the present invention; and FIG. 2 is a perspective view of a sheet of glass with the laser light output from the laser system shown in FIG. 1 entering an edge thereof.

DETAILED DESCRIPTION OF THE INVENTION

With reference to FIG. 1, a laser 2 includes a laser tube 4 positioned between a fully reflective mirror 6 and a half-reflective mirror 8. A phase modulator 10 is positioned between laser tube 4 and half-mirror 8. Another phase modulator 12 is positioned on a side of half-mirror 8 opposite phase modulator 10. Laser tube 4, mirror 6, half-mirror 8 and phase modulators 10 and 12 have their axes positioned coaxially.

An RF oscillator 14 is connected to supply phase modulator 10 with control signals which cause phase modulator 10 to control the phase of laser light passing therethrough.

A phase shifter 16 is connected between oscillator 14 and phase modulator 12. Phase shifter 16 phase shifts the control signals output by oscillator 14 and supplies the phase shifted control signals to phase modulator 12 for shifting the phase of laser light passing therethrough. Laser tube 4, mirror 6, half-mirror 8, phase modulators 10 and 12, RF oscillator 14 and phase shifter 16 co-act to form a signal source that produces an output signal in the form of output laser light 18 having a frequency corresponding to a natural or sympathetic vibration frequency of the molecules forming a body, such as quartz or silica glass.

With reference to FIG. 2 and with continuing reference to FIG. 1, the phase of output laser light 18 can be controlled by phase modulators 10 and 12 under the control of oscillator 14 and phase shifter 16 so that when output laser light 18 impinges on a sheet of glass 20, the phase of output laser light 18 matches the phase of the molecules forming sheet of glass 20 vibrating at their sympathetic or natural vibration frequency. Laser tube 4, mirror 6, half-mirror 8, phase modulators 10 and 12, oscillator 14 and phase shifter 16 collectively form a super mode-locking laser. Oscillator 14 and phase shifter 16 can be formed from the same materials so as to perfectly respond to each other's signals.

Output laser light 18 having the same frequency and phase as the molecules forming sheet of glass 20 urges the molecules of sheet of glass 20 to vibrate at their sympathetic or natural vibration frequency notwithstanding these molecules receiving energy from other external sources by way of radiation, conduction or convection. More specifically, in the absence of output laser light 18 impinging thereon, sheet of glass 20 has a first thermal resistance to a flow of heat from a heat source 22 positioned on one side of sheet of glass 20 to a heat sink 24 positioned on the other side of sheet of glass 20, where heat source 22 is at a higher temperature than heat sink 24. In response to output laser light 18 impinging on sheet of glass 20, the molecules of sheet of glass 20 are urged to vibrate at their sympathetic or natural vibration frequency thereby changing the thermal resistance of sheet of glass 20 to a second thermal resistance which is greater than the first thermal resistance. Hence, when the molecules of sheet of glass 20 are excited by output laser light 18, the thermal resistance of sheet of glass 20 increases thereby increasing the ability of sheet of glass 20 to obstruct the flow of heat from heat source 22 to heat sink 24.

In the illustrated embodiment, output laser light 18 forms a blanket oscillation field which extends through sheet of glass 20 parallel to a planar surface thereof. However, this is not to be construed as limiting the invention. In a conventional sheet of glass, this planar surface is one of the outward facing surfaces of the sheet of glass. The energy conveyed in the blanket oscillation field is charged in the manner of sympathetic vibration of molecular energy. This energy will continue unabated providing the output laser light 10 is of constant power. This vibration will artificially induce a vibration in the molecular structure of quartz or silica glass crystals which will not be varied by any other external source, i.e., radiation, conduction or convection currents. Stated differently, the impressed sympathetic vibration avoids changes in the natural vibration frequency of the molecules of sheet of glass 20 due to energy transfer. This change is essential and co-existent for any transfer of energy. This "wall of a force field" can be maintained in areas of any size or dimension in sheet of glass 20.

In operation, output laser light 18 enters sheet of glass 20 through an edge thereof in a direction substantially parallel to one of the planar surfaces of sheet of glass 20. Output laser light 18 causes molecules of sheet of glass 20 in the path of output laser light 18 to oscillate or vibrate at their sympathetic vibration frequency. This oscillation causes a chain reaction in the molecules of sheet of glass 20 which, in turn, creates a homogeneous effect of oneness for the entire volume of sheet of glass 20. The constancy of the procedure is achieved because of the creation of the super mode-locking laser having maximum output with no distortion. This chain reaction is a unique property of silica material. Other materials can achieve this constancy, but silica is the simplest to achieve the proper vibration. Once the resonance begins, it propagates in all directions instantly without any limits of distance or space. This process occurs inherently in nature and is the basic and ultimate release of energy in unified fields.

Output laser light 18 having the same frequency and phase as the molecules of sheet of glass 20 forms a blanket oscillation field, or "force field", that forces the molecules of sheet of glass 20 to vibrate at their sympathetic vibration frequency whereupon a flow of energy through sheet of glass 20 from heat source 22 to heat sink 24 is obstructed or rejected. When sheet of glass 20 is installed in a structure, like a building, forcing the molecules of sheet of glass 20 to vibrate at their sympathetic vibration frequency in the above-described manner enables sheet of glass 20 to obstruct the flow of energy impinging thereon via radiation, conduction or convection. This can result in energy savings due to reduced need to heat or cool the interior air of the structure in response to radiation, conduction or convection currents flowing into the structure through sheet of glass 20.

The invention has been described with reference to the preferred embodiment. Obvious modifications and alterations will occur to others upon reading and understanding the preceding detailed description. For example, it is believed that slight variances of the frequency and/or phase of output laser light 18 with respect to the natural vibration frequency and/or phase of the molecules forming the object, e.g., sheet of glass 20, will still increase the thermal resistance of the object, but just not as much. It is intended that the invention be construed as including all such modifications and alterations insofar as they come within the scope of the appended claims or the equivalents thereof.

The invention claimed is:

1. A method of obstructing a flow of energy through an object comprising:
    (a) providing a signal source that produces an output signal having a frequency the same or substantially the same as a sympathetic vibration frequency of molecules forming the object; and
    (b) directing the output signal toward the object whereupon, in response to interaction with the output signal, the molecules of the object vibrate at their sympathetic vibration frequency thereby obstructing a flow of energy therethrough, wherein the signal source includes a laser tube positioned to propagate a laser light emitted from opposite ends thereof toward a fully reflective mirror and a half-reflective mirror, a first phase modulator positioned in the path of the laser light between the laser tube and the half-reflective mirror, a second phase modulator positioned in the path of the laser light on a side of the half-reflective mirror opposite the first phase modulator and control means for controlling the first and second phase modulators whereupon the laser light propagating from the second phase modulator away from the half-reflective mirror has the same phase as the phase of the molecules forming the object.

2. The method of claim 1, wherein the object is a sheet of glass having a pair of oppositely facing surfaces.

3. The method of claim 2, wherein step (b) includes causing the laser light to propagate through the sheet of glass between the surfaces in a direction substantially parallel to at least one of the surfaces.

4. The method of claim 2, wherein the flow of energy is obstructed from flowing between the surfaces of the sheet of glass.

5. The method of claim 2, wherein the laser light produces in the sheet of glass a blanket oscillation field that extends through the sheet of glass parallel to at least one of the surfaces thereof.

6. The method of claim 1, wherein the energy includes at least one of radiation, conduction and convection.

7. The method of claim 1, wherein the control means includes an oscillator for producing an oscillator signal and a phase shifter for phase shifting the oscillator signal, the first and second phase modulators responsive to the oscillator signal and the phase shifted oscillator signal, respectively, for adjusting the laser light whereupon the phase of the laser light propagating from the second phase modulator away from the half-reflective mirror is in phase with the molecules forming the object.

8. A system for obstructing a flow of energy comprising:
   an object interposed between a heat source and a heat sink, where the heat source is at a higher temperature than the heat sink and the object has a first thermal resistance to the flow of heat between the heat source and the heat sink; and
   means for exciting molecules of the object to vibrate at or substantially at their natural frequency whereupon, in response to said vibration, the thermal resistance of the object increases to a second thermal resistance, wherein the exciting means includes:
   a laser for outputting a laser light having the same frequency as the natural frequency of the molecules of the object;
   means for reflecting at least part of the laser light; and
   means for adjusting the phase of the laser light whereupon the laser light interacting with the object is in phase with the phase of the molecules of the object.

9. The system of claim 8, wherein the flow of heat occurs via at least one of radiation, conduction and convection.

10. The system of claim 8, wherein the object is a sheet of glass.

11. The system of claim 8, wherein the adjusting means includes:
    an oscillator outputting an oscillator signal; and
    a phase modulator responsive to the oscillator signal.

12. The system of claim 8, wherein the reflecting means includes:
    a full mirror positioned at one end of the laser for reflecting light output thereby back into the laser; and
    a half-mirror positioned at the other end of the laser for reflecting part of the light output thereby back into the laser and for partially passing laser light impinging thereon.

* * * * *